(12) United States Patent
Imai (10) Patent No.: US 7,495,756 B2
(45) Date of Patent: Feb. 24, 2009

(54) PATTERN INSPECTION APPARATUS

(75) Inventor: Shinichi Imai, Tokyo (JP)

(73) Assignee: Advanced Mask Inspection Technology Inc., Kawasaki-shi (JP)

( * ) Notice: Subject to any disclaimer, the term of this patent is extended or adjusted under 35 U.S.C. 154(b) by 151 days.

(21) Appl. No.: 11/299,848

(22) Filed: Dec. 13, 2005

(65) Prior Publication Data

US 2007/0064223 A1    Mar. 22, 2007

(30) Foreign Application Priority Data

Sep. 20, 2005    (JP)    ............... 2005-271306

(51) Int. Cl.
  *G01N 21/00*    (2006.01)
(52) U.S. Cl. ................. 356/237.1; 356/237.2
(58) Field of Classification Search ........... None
  See application file for complete search history.

(56) References Cited

U.S. PATENT DOCUMENTS

| | | | |
|---|---|---|---|
| 5,745,284 A | | 4/1998 | Goldberg et al. |
| 6,373,869 B1 | | 4/2002 | Jacob |
| 6,819,416 B2 * | | 11/2004 | Maeda et al. ............ 356/237.2 |
| 6,831,737 B2 * | | 12/2004 | Uto et al. ................ 356/237.4 |
| 7,019,850 B2 * | | 3/2006 | Finarov .................... 356/630 |
| 2002/0054613 A1 | | 5/2002 | Kang |
| 2003/0095251 A1 * | | 5/2003 | Maeda et al. ............ 356/237.2 |
| 2006/0012780 A1 * | | 1/2006 | Nishiyama et al. ....... 356/237.4 |
| 2006/0222372 A1 * | | 10/2006 | Spinelli et al. ............ 398/183 |

FOREIGN PATENT DOCUMENTS

| | | |
|---|---|---|
| JP | 8-76359 | 3/1996 |
| JP | 10-341054 | 12/1998 |

(Continued)

OTHER PUBLICATIONS

T. Tojo, et al., "Advanced mask inspection optical system (AMOS) using 198.5-nm wavelength for 65-nm (hp) node and beyond: system development and initial state D/D inspection performance", Proceedings of SPIE Reprint, 24th Annual BACUS Symposium on Photomask Technology, vol. 5567, SPIE paper # 5567-110, Sep. 14-17, 2004, pp. 1011-1023 with cover page.

(Continued)

*Primary Examiner*—Michael P Stafira
(74) *Attorney, Agent, or Firm*—Oblon, Spivak, McClelland, Maier & Neustadt, P.C.

(57) ABSTRACT

A pattern inspection apparatus is disclosed, which includes a first laser light source for emission of first laser light having a first wavelength, a second laser light source for emission of second laser light having a second wavelength, and a deep ultraviolet (DUV) light source for emission of DUV light with a wavelength of less than or equal to 266 nm based on the first laser light and the second laser light. A first optical fiber is provided for connecting between the first laser light source and the DUV light source. A second optical fiber is for connection between the second laser light source and the DUV light source. The apparatus also includes a pattern inspection unit with the DUV light source being built therein, for inspecting a workpiece pattern being tested by using the DUV light as illumination light therefor.

16 Claims, 6 Drawing Sheets

FOREIGN PATENT DOCUMENTS

JP        2001-83557      3/2001
JP        2005-241290     9/2005

OTHER PUBLICATIONS

H. Kawai, et al., "UV light source using fiber amplifier and nonlinear wavelength conversion", 23rd Annual Conference on Lasers and Electro-Optics (CLEO 2003) and the 11th Quantum Electronics and Laser Science Conference (QELS 2003), Paper No. CTuT4, 2 Pages.

U.S. Appl. No. 11/523,027, filed Sep. 19, 2006.
U.S. Appl. No. 11/523,028, filed Sep. 19, 2006.
U.S. Appl. No. 11/299,848, filed Dec. 13, 2005, Imai.
"Mobius licenses Harvard UV laser technology", Laser Focus World, Feb. 4, 2008, p. 39.

* cited by examiner

PATTERN INSPECTION APPARATUS

CROSS-REFERENCE TO RELATED APPLICATION

This application is based upon and claims the benefit of priority from prior Japanese Patent Application No. 2005-271306, filed on Sep. 20, 2005, the entire contents of which are incorporated herein by reference.

BACKGROUND OF THE INVENTION

1. Field of the Invention

The present invention relates generally to pattern inspection technologies and, more particularly, to pattern inspection techniques for inspecting a semiconductor fabrication-use workpiece pattern for defects. This invention also relates to an apparatus for inspecting lithography masks for defects, which are adaptable for use in the manufacture of semiconductor devices and liquid crystal display (LCD) panels.

2. Related Art

In recent years, with the quest for higher integration and larger capacity of large-scale integrated (LSI) circuits, semiconductor devices are becoming narrower in circuit linewidth required. These semiconductor devices are fabricated by using an original or "master" plate with a circuit pattern formed thereon (also called a photomask or a reticle as will be generically referred to as a mask hereinafter) in a way such that the pattern is exposure-transferred by reduced projection exposure equipment, known as a stepper, onto a target wafer to thereby form thereon a circuit. Hence, for the manufacture of a mask to be used to transfer such ultrafine circuit pattern onto wafers, pattern photolithography equipment is used, which is capable of "drawing" microcircuit patterns. Such pattern exposure equipment is also employable in some cases to directly draw or "image" a circuit pattern onto wafers. As for the pattern exposure equipment, an attempt is made to develop exposure tools using an electron beam or laser beam.

Improving manufacturing yields is inevitable for the microfabrication of LSI chips which entail increased production costs. Currently, circuit patterns of LSIs, such as 1-gigabit class dynamic random access memories (DRAMs), are becoming on the order of nanometers (nm), rather than submicron order. One major factor for reducing yields must be pattern defects of a mask as used when an ultrafine pattern is exposed and transferred onto semiconductor wafers by photolithography techniques. As LSI patterns to be formed on semiconductor wafers are further miniaturized in recent years, the size dimensions that must be detected as pattern defects became much smaller than ever before. Thus, a need is felt to achieve further increased accuracy of the pattern inspection apparatus operable to inspect the LSI fabrication-used pattern-transfer mask for defects.

Incidentally, with recent advances in multimedia technologies, LCD panels are becoming larger in substrate size, up to 500 mm×600 mm or more, and finer in pattern of thin film transistors (TFTs) as formed on liquid crystal substrates. This larger/finer trend requires an ability to inspect ultrasmall pattern defects in a wide range. For this reason, it is an urgent challenge to develop an advanced workpiece inspection apparatus capable of efficiently inspecting defects of photomasks in a short time period, which are for use in the manufacture of such large-area LCD patterns and large-screen LCD panels.

Here, in currently available pattern inspection tools, it is known to perform inspection by comparing the optical image of a pattern on a workpiece, such as a lithography mask or else, which image is sensed by using a magnifying optical system at a specified magnification, to either design data or a sensed optical image of an identical pattern on the workpiece. This approach is disclosed, for example, in JP-A-8-76359.

Examples of pattern inspection methodology include a "die to die" inspection method and a "die to database" inspection method. The die-to-die inspection is for comparing together optical images as sensed from identical pattern elements at different locations on the same mask. The die-to-database inspection is usually performed using an exposure device for drawing or "imaging" a pattern on a mask and an inspection device. Typically this inspection has the steps of receiving computer-aided design (CAD) data indicative of a designed pattern, converting the CAD data to pattern draw data having a format appropriate for data input to the imaging device, inputting the converted data to the inspection device, causing it to generate a reference image based thereon, receiving measured data indicative of the optical image of a pattern under testing as obtained by pickup of this pattern, and then comparing the optical image to the reference image to thereby inspect the under-test pattern for defects. The inspection method for use in such apparatus, the workpiece is mounted on a stage, which moves to permit light rays to scan a surface of the workpiece for execution of the intended inspection. A light source and its associated illumination optical lens assembly are used to emit and guide the light to fall onto the workpiece. The light that passed through the workpiece or reflected therefrom travels via the optics to enter a sensor so that a focussed optical image is formed thereon. This optical image is sensed by the sensor and then converted to electrical measurement data, which will be sent to a comparator circuit. After position-alignment between images, the comparator circuit compares the measured data to reference image data in accordance with an adequate algorithm. If these fail to be matched, then determine that pattern defects are present.

As previously stated, the quest for higher performance of semiconductor devices results in minimization of feature sizes and in increase in integration densities of chips. This trend in turn requires inspection equipment to offer higher resolutions. To this end, a need is felt to shorten the wavelength of illumination light. It is thus required to employ a laser light source having an inspection wavelength of deep ultraviolet (DUV) region. The currently available semiconductor road map suggests that for nodes of 90 nanometers (nm) or beyond, it becomes necessary to use illumination light with its inspection wavelength of 266 nm or less.

While it is desirable to use continuous wave light as the illumination light of inspection apparatus in order to permit a pattern image to accurately focus on a sensor, it is a must in order to obtain a continuous wave light source to perform wavelength conversion of a continuously oscillating long-wavelength laser beam for use as a fundamental wave to a wave having a shorter wavelength. More specifically, it is required to perform summed frequency generation while letting a plurality of continuous output laser beams of longer wavelengths than a prespecified wavelength being as the fundamental wave. However, such wavelength conversion is inherently a nonlinear process, and thus requires the use of high electric fields for enhancing the conversion efficiency. Additionally in view of the fact that the continuous oscillation essentially gives low electric fields, a special technique is needed for such wavelength conversion. Here, in order to increase the electric field intensity in a nonlinear medium, it is a must to employ a resonator structure of the type confining the fundamental wave in a nonlinear crystal. An example of the resonator used for sum frequency generation is an intracavity resonator having its laser amplifying medium as installed within the resonator. Another example is an extra-cavity resonator with a fundamental wave generation source being external to the resonator for the sum frequency generation use. An example of a continuous wave light source employing the resonator structure is disclosed, for example, in JP-A-10-341054, which is designed to emit 193-nm wavelength continuous wave light.

Unfortunately, the advantage of prior known continuous wave light source does not come without accompanying penalties of unwanted size increases. This can be said because these are required to use a large-size argon laser at part of a fundamental wave light source and also introduce resonators of the type stated above in order to emphasize fundamental wave electric fields. Another problem faced with the prior art lies in the risk of disturbance susceptibility as such resonators are relatively long in optical path for spatial propagation. A further problem is that the use of complicated configuration necessitates workers to consume much time to do maintenance services. Obviously a need for frequent maintenance works forces resonators to have a limited length of uninterrupted operation time period.

Another further problem encountered with the prior art resonator-associated light sources is that their complicated structures and increased size dimensions make it difficult to achieve installation into inspection equipment. If such installation is enabled, it still remains difficult to integrate the light source with the optics of inspection equipment. For these reasons, the light source is usually designed so that it is laid out at locations adjacent or next to its associative inspection apparatus or, alternatively, mounted spaced apart from the optics of inspection equipment. In this case, illumination light as given off from the light source is typically designed to travel along a long optical path prior to arriving at the optics of inspection apparatus, through spatial propagation with complicated combinations of mirrors and lenses. This poses a problem as to increased affectability of vibrations occurring due to motions of a wafer/mask support stage in the inspection apparatus. This in turn compels manufacturers to exert strenuous efforts for maintenance management of optical axes. Additionally, the difficulty in integrating the light source with the inspection apparatus badly behaves to limit designs of such inspection apparatus.

Another known approach is to employ as the inspection tool light source a short-wave length laser light source using a high electric field-obtainable pulsed laser beam. Even in this approach, it is still difficult to build the laser light source per se in the inspection equipment. Even when such is enabled, it is difficult to integrate it with the optics of inspection equipment. This brings similar results—i.e., the laser light source must be laterally disposed adjacent to the inspection equipment or spaced part from the optics thereof, resulting in output illumination light of the light source being forced to propagate along an elongate optical path prior to reaching the inspection equipment optics through spatial propagation with complexity of mirrors and lenses combined together, which causes a vibration influence problem similar to that stated supra. Thus, this laser light source also suffers from similar disadvantages to those stated above—i.e., the need for taking much time to do optical-axis maintenance management and limited design of inspection equipment.

Short-wavelength laser light sources using the high electric field-acquirable pulse laser light include a pulse light source with an ability to obtain a 193-nm pulsed laser beam by eight-harmonic generation from 1.5-micrometer light, examples of which are disclosed in JP-A-2001-83557 and the 23rd Annual Conference on Lasers and Electro-Optics (CLEO 2003) and the 11th Quantum Electronics and Laser Science Conference (QELS 2003), Paper No. CTuT4. An inspection tool with a built-in 199-nm light source is taught, for example, from the 24th Annual BACUS Symposium on Photomask Technology (September, 2004, Monterey, Calif., USA), Paper No. SPIE5567-110.

It has been stated that prior known light sources for obtaining the illumination light of pattern inspection apparatus are faced with various problems.

BRIEF SUMMARY OF THE INVENTION

It is an object of this invention to provide a pattern inspection apparatus of high reliability capable of avoiding the problems faced with the prior art and offering robustness against vibrations.

In accordance with one aspect of this invention, a pattern inspection apparatus includes a light source for emission of a fundamental wave, a wavelength conversion unit operative to convert the fundamental-wave light to have a wavelength of less than or equal to 266 nanometers (nm), and an optical fiber for connection between the light source and the wavelength conversion unit. The wavelength conversion unit is built in an apparatus body. The pattern of a workpiece being tested is inspected with output light of the wavelength conversion unit being as illumination light.

In accordance with another aspect of the invention, a pattern inspection apparatus includes a first laser light source for emission of first laser light having a first wavelength, a second laser light source for emission of second laser light having a second wavelength different from the first wavelength, and a deep ultraviolet (DUV) light source for emission of DUV light with a wavelength of less than or equal to 266 nm based on the first laser light and the second laser light. The inspection apparatus also includes a first optical fiber for connection between the first laser light source and the DUV light source, and a second optical fiber for connection between the second laser light source and the DUV light source. The apparatus further includes a pattern inspection unit with the DUV light source being built therein, for inspecting the pattern of a workpiece being tested while using as illumination light the DUV light as emitted from the DUV light source.

In accordance with still another aspect of the invention, a pattern inspection apparatus is such that a pattern of a workpiece being tested is inspected by using, as illumination light, second summed frequency based on first summed frequency light which is generated by using a four-time higher harmonic wave of first laser light having a wavelength ranging from 1,064 to 1,065 nm and second laser light with its wavelength of from 1557 to 1571 nm, and the second laser light.

In accordance with a further aspect of the invention, a pattern inspection apparatus is such that a pattern of a workpiece under testing is inspected by using, as illumination light from the sum frequency generation of the first pulse laser having its wavelength ranging from 1064 to 1065 nm and the second pulse laser with its wavelength of 1557 to 1571 nm.

DETAILED DESCRIPTION OF THE INVENTION

Embodiment 1

Figure 1:
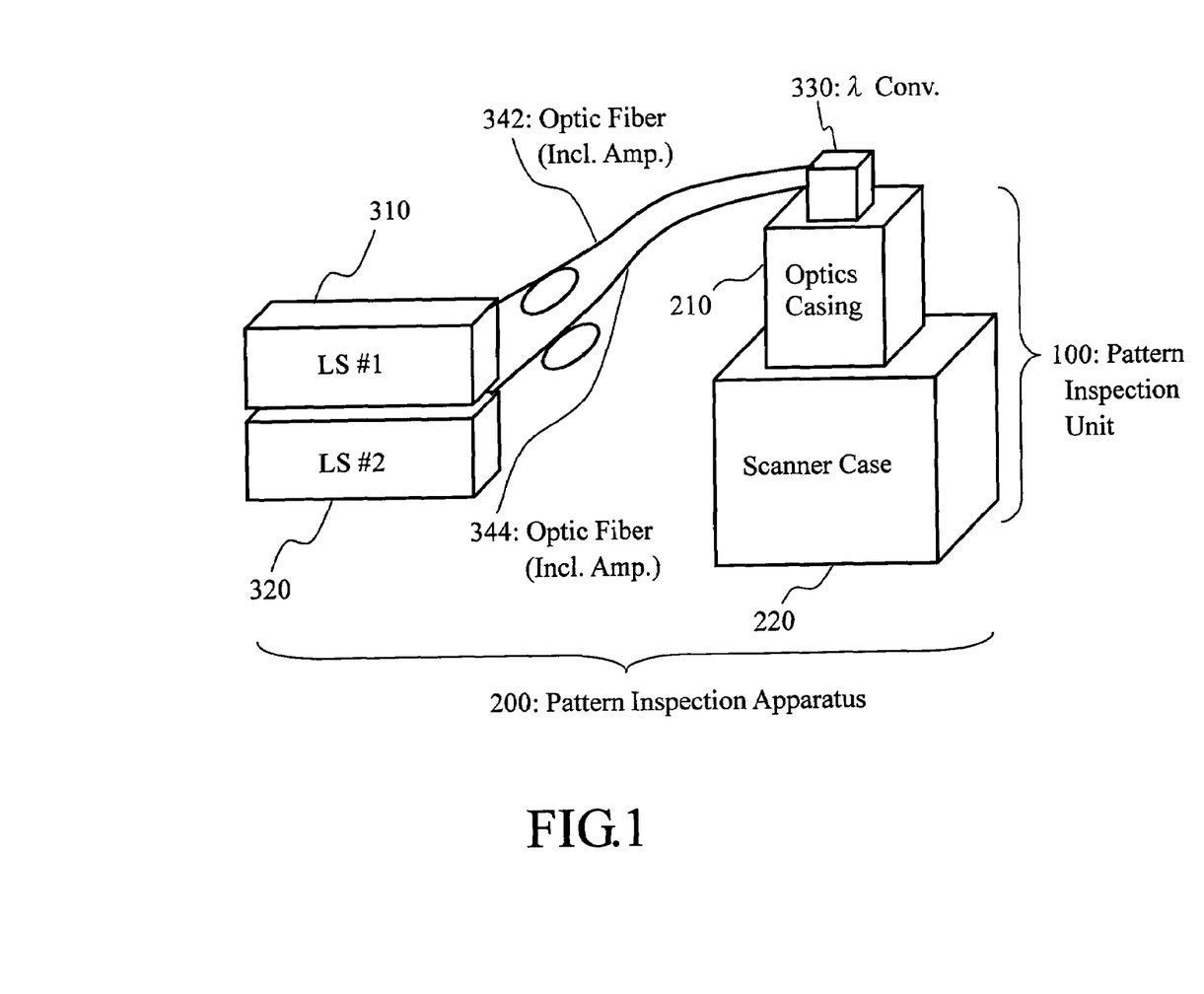
FIG. 1 is a diagram schematically showing an overall arrangement of a pattern inspection apparatus in accordance with an embodiment 1 of this invention.

Referring to FIG. 1, there is shown an entire structure of a pattern inspection apparatus 200 in an embodiment 1.

As shown herein, the pattern inspection apparatus 200 is arranged to include a pattern inspection unit 100, a couple of first and second fundamental wave light source modules 310 and 320, a wavelength conversion unit 330, and optical fiber cables 342 and 344. The pattern inspection unit 100 has a housing 210 which contains an assembly of optical lenses and mirrors and a housing 220 with a scanner unit included or "packed" therein. The wavelength (λ) converter unit 330 is built in pattern inspection unit 100—specifically, in the optics housing 210. Preferably the λ converter 330 is integrally combined with optics housing 210. The first and second fundamental-wave light sources 310 and 320 are physically separated from the λ converter 330 so that light sources 310, 320 are connected thereto by optical fiber cables 342, 344, respectively. With the light-source/λ-converter separation feature, it is possible to install the λ converter 330—this is an example of the deep ultraviolet (DUV) light source for emission of the illumination light as used in the pattern inspection apparatus 200—in the pattern inspection unit 100, in particular in the optics housing 210 of inspection unit 100. Enabling installation of λ converter 330 in optics housing 210 makes it possible to shorten an optical path for spatial propagation. This makes it possible to reduce optical-axis deviations otherwise occurring due to vibrations applicable from a scanner housing 220 to be later described. Thus it is possible to minimize unwanted influenceability against workpiece inspection.

Figure 2:
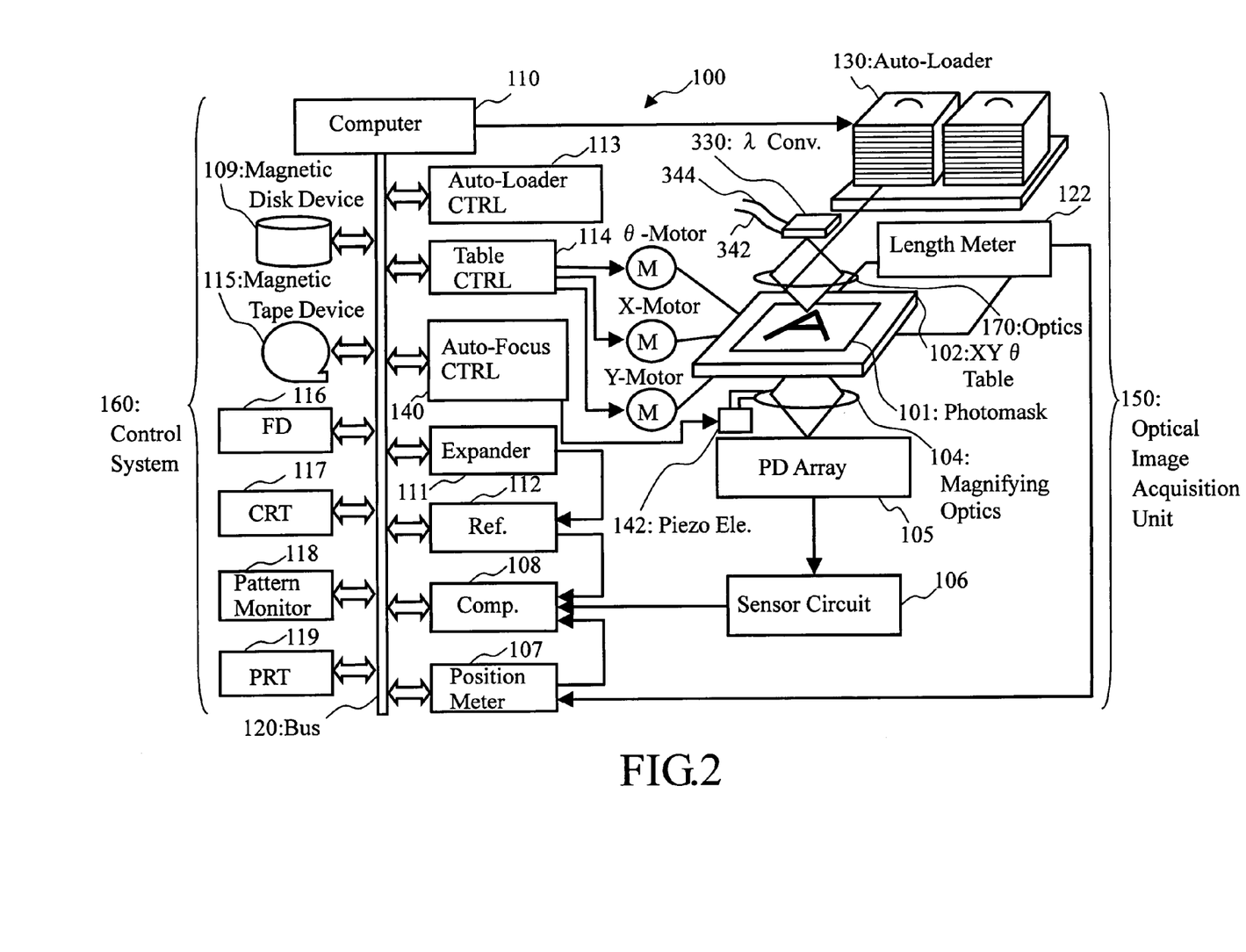
FIG. 2 is a diagram showing a configuration of main part of the inspection apparatus of the embodiment 1.

See FIG. 2, which shows an internal configuration of pattern inspection apparatus in the embodiment 1.

In FIG. 2, the workpiece pattern inspection unit 100 in the pattern inspection apparatus 200 is operable to inspect a workpiece for defects. A typical example of the workpiece is a substrate under manufacture, such as a photomask or wafer or else. The inspection unit 100 is generally made up of an optical image acquisition unit 150 and control circuitry 160. The image acquisition unit 150 includes an illumination optical system 170 as disposed in the optics housing 210 of FIG. 1, an XYθ-axis table 102 in the scanner housing 220, a magnifying optical lens assembly 104, photodiode (PD) array 105, sensor circuit 106, laser-assisted length measurement system (namely, laser length meter) 122, automatic loader mechanism 130, and a piezoelectric device 142. The control circuitry 160 includes a computer 110 acting as a system controller. This control computer 110 is connected via a data transmission bus 120 to a position circuit 107, comparison circuit 108, expansion circuit 111, reference circuit 112, autofocussing control circuit 140, auto-loader control circuit 113, table control circuit 114, magnetic disk device 109, magnetic tape device 115, flexible disk (FD) device 116, cathode ray tube (CRT) display 117, pattern monitor 118 and printer 119. The XYθ table 102 is driven by an X-axis motor, Y-axis motor and θ-axis motor. Note here that in FIG. 1, illustration of those parts or components other than the constituent members required for the explanation of this embodiment 1 is eliminated. It would readily occur to skilled persons that the pattern inspection apparatus 200 is usually designed, for practical implementation, to include such other necessary arrangements.

Figure 3:
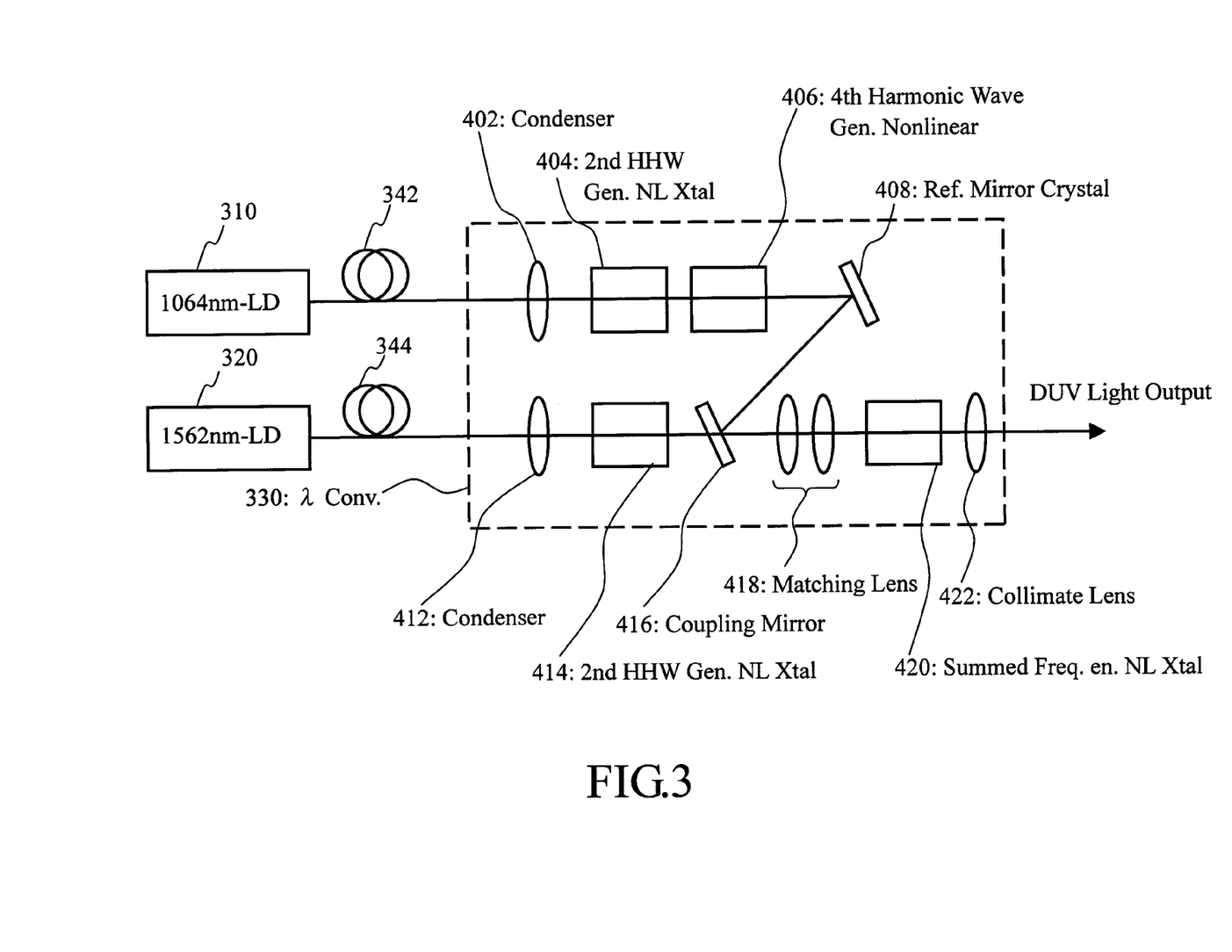
FIG. 3 depicts an internal structure of a wavelength converter unit in the inspection apparatus, for explanation of a scheme for emitting illumination light.

FIG. 3 shows schematically an internal configuration of the wavelength (λ) converter unit 330 in the embodiment 1, for explanation of a process for producing illumination light.

In FIG. 3, the first fundamental wave light source 310, which is one example of the laser light source as claimed, is arranged to emit laser light (first fundamental wave) having a wavelength of 1,064 to 1,065 nm (recited to be "1064 nm" hereafter). An example of the first fundamental wave light source 310 is a semiconductor laser, including a laser diode (LD) which is labeled as "1064 nm-LD" in FIG. 3. The semiconductor laser is current-driven to emit laser light. By causing a pulsate drive current to flow in the fundamental wave light source 310, the light source produces a beam of pulsed laser light. An example is that a semiconductor laser with its average output power of 100 milliwatts (mW) is used during a continuous operation and driven by a pulsate current having a pulse frequency of 2 megahertz (MHz) with its pulse width of 2 nanoseconds (ns). In this case, resultant laser light has a pulse width of 1.5 ns. Its average output power obtained at this time was 0.3 mW.

The optical fiber cable 342 functions as a transmission fiber and also acts as an amplifier. More specifically, upon entry of pump light from a pump laser (not shown), the fiber 342 performs amplification of the 1064-nm laser light. For example, introduction of the pulsed laser light with average output power of 0.3 mW into the amplifying optical fiber results in obtainment of outgoing laser light with its average output power of 5 W. The amplifiable fiber may be a quartz fiber with ytterbium (Yb) doped thereinto as active material, although this invention should not be limited thereto and other dopants may be contained therein. The optic fiber 342 is for connecting between the first fundamental wave light source 310 and the converter unit 330.

While exclusive-use or "dedicated" parts are used for connection of respective optical systems, detailed explanations of those other than essential arrangements necessary for explanation of this embodiment will be eliminated herein. The optical components and their connectors along with electrical parts and amplifiable fiber excitation semiconductor laser plus its drive source are received or "packed" together in the first fundamental wave light source 310. In all of these optical components polarizations are maintained. An optical output of light source 310 is transferred by optic fiber 342 to λ converter 330.

The second fundamental wave light source 320 for use as an example of the laser light source is designed to emit laser light (second fundamental wave) having a wavelength of 1,557 to 1,571 nm (recited to be "1562 nm" hereafter). An example of the second light source 320 is a semiconductor laser—typically, a laser diode (LD) labeled as "1562 nm-LD" in FIG. 3. Letting a pulsate drive current flow in this light source 320 results in production of a beam of pulsed laser light. An example is that a semiconductor laser with its average output power of 80 mW is used during a continuous operation and is driven by a 2-MHz pulsate current with its pulse width of 2 ns; in this case, resultant laser light has a pulse width of 1.5 ns. Its average output power obtained at this time was 0.24 mW. With both this laser and the above-stated 1064 nm-LD 310 being driven at a time, it was possible for it to operate with jitters of 120 ps or less.

The second optical fiber cable 344 functions as a transmission fiber and also serves as an amplifier. More specifically, upon entry of pump light from its associated pump laser (not shown), the fiber 344 amplifies the 1562-nm laser light. For example, introduction of pulsed laser light with average output power of 0.24 mW into the amplifying optic fiber results in obtainment of laser light with its average output power of 5 W. The amplifier fiber may be a quartz fiber with erbium (Er) doped thereinto as active material, although not specifically limited thereto and other dopants may be contained therein. The optic fiber 344 is for optical coupling between the second fundamental wave light source 320 and λ converter 330.

While dedicated optical tele-communication parts are used for connection of respective optical systems, detailed explanations of those other than essential arrangements necessary for explanation of this embodiment will be omitted here. The optical components and their connectors along with electrical parts and amplifiable fiber excitation semiconductor laser plus its drive source are packed together in the second fundamental wave light source 320. All of these optical components are with polarization maintained. Output light of light source 320 is sent forth by optical fiber 344 to the λ converter unit 330.

The λ converter 330, which exemplifies the deep-UV (DUV) light source, performs generation of DUV light with a wavelength of 266 nm or less—e.g., 198 nm—by wavelength conversion based on the 1064-nm laser light and 1562-nm laser light. An exemplary procedure for such λ conversion is as follows.

What is done first is to generate fourth-harmonic wave light. The incoming 1064-nm laser light from optical fiber 342 is collected by a collection lens or "condenser" 402, resulting in an increase in electrical field. This permits the condensed light to enter a nonlinear crystal 404, which is for generation of second harmonic wave of the 1064-nm wavelength laser light, thereby producing laser light with its wavelength of 532 nm, which is for use as the second harmonic wave of the 1064-nm wavelength laser light. Then, guide this 532-nm wavelength laser light to enter a nonlinear crystal 406, which is for generation of fourth harmonic wave, resulting in production of laser light having a wavelength of 266 nm, which is for use as the fourth harmonic wave of the 1064-nm wavelength laser light. Preferably the second harmonic wave-producing nonlinear crystal 404 is comprised of potassium titanyl phosphate ($KTiOPO_4$ or KTP), whereas the fourth harmonic wave creating nonlinear crystal 406 is made of beta barium borate ($\beta$-$BaB_2O_4$ or BBO), although any other similar suitable crystal materials are employable as far as these are optically transparent at the wavelength of interest and offer phase matchablilities in respective wavelength conversion processes.

For the 1562-nm wavelength laser light, second-harmonic light is created in a way which follows. The incoming 1652-nm laser light from optical fiber 344 is collected by a condenser lens 412, resulting in an increase in electric field. This allows the resultant light to enter a nonlinear crystal 414, which is for production of second harmonic wave of the 1562-nm wavelength laser light, thereby generating laser light with its wavelength of 781 nm, which is for use as the second harmonic wave of the 1562-nm wavelength laser light. Preferably the second-harmonic generation nonlinear crystal 414 is made of lithium triborate ($LiB_3O_5$ or LBO), although any other suitable crystals are usable as far as they are transparent at the wavelength of interest while offering excellent phase matchability in the process of wavelength conversion.

Inside the λ converter 330, in succession to the above-noted wavelength conversion, the 266-nm wavelength laser light, which is the fourth harmonic wave light of the 1064-nm wavelength laser light, is reflected at a reflector mirror 408 to reach a coupler mirror 416, at which the reflected light is combined with the 781-nm wavelength laser light that is the second harmonic wave light of the 1562-nm wavelength laser light. Then, the combined light is guided to travel through a matching lens assembly 418 to coaxially enter a sum frequency generation-use nonlinear crystal 420 in the form of a single collected beam of light, thereby producing as the intended DUV light a beam of 198-nm wavelength laser light with the sum frequency of the both. Using this scheme may enhance the conversion efficiency. Preferably the nonlinear crystal 420 as used here is made of BBO, although other equivalent materials are employable as far as these are transparent at this wavelength while offering excellent phase matchability in the process of wavelength conversion. The light obtained is then guided to progress via a collimate lens 422, thereby providing laser light with its wavelength of 198 nm, which is then forced to enter the illumination-light optical system 170 as the illumination light of pattern inspection apparatus 200. This light is for use during inspection of the pattern of a photomask 101, i.e., the workpiece being tested, in a way as will be described later.

Figure 4:
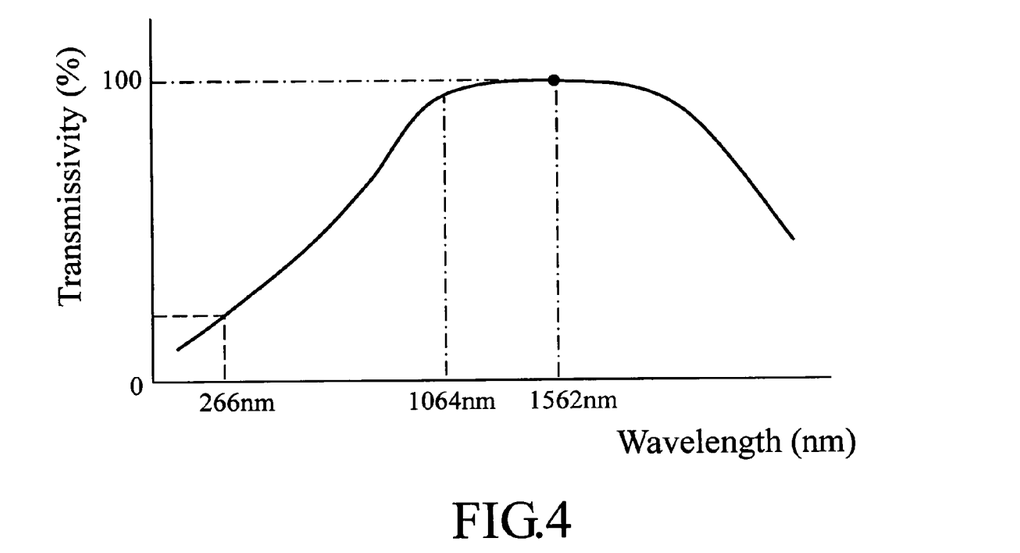
FIG. 4 is a graph showing a plot of laser-light transmissivity as a function of wavelength in an optical fiber cable.

FIG. 4 shows a plot of transmissivity versus wavelength in optical fibers.

As apparent from FIG. 4, illumination light having an inspection wavelength of 266 nm or less which is required for 65-nm nodes is extremely low in transmissivity in optical fiber. In contrast, the laser light with its wavelength of 1562 nm as used in this embodiment exhibits almost 100 percent (%) of transmissivity. Alternatively the 1064-nm wavelength light is approximately 100% in transmissivity although this is somewhat less than that of the 1562-nm wavelength light. Hence, using the 1064-nm wavelength laser light and 1567-nm laser light in combination as the fundamental waves makes it possible to use optical fiber cables for the light source device. This makes it possible to separate or split the first and second fundamental wave light sources 310 and 320 and the λ converter 330. It is thus possible to dispose the light sources 310, 320—these are large in size and less in robustness against mechanical vibrations—at locations spaced far from the body of the pattern inspection apparatus 200, thereby to ensure that they are free from direct reception of inspection apparatus vibrations. A further advantage of the use of optical fibers lies in an ability to avoid spatial propagation in a route spanning from the fundamental wave light sources 310, 320 up to λ converter 330. Thus it is possible to prevent or at least greatly reduce optical axis deviations otherwise occurring due to vibrations and/or disturbances of the pattern inspection apparatus 200.

In addition, by using pulse waves for both of the fundamental waves of first and second laser light sources 310 and 320, it is possible to preclude the necessity for providing resonators in the λ converter unit 330. This makes it possible to reduce built-in parts in number, thereby enabling λ converter 330 to decrease in size. The compact 30 and light weight features of λ converter 330 permit this converter 330 of small occupation volume to be integrally built in the pattern inspection unit 100—especially, packed in the optics housing 210 of inspection unit 100 for direct coupling with the optics thereof. The integration of λ converter 330 in optics housing 210 makes it possible to shorten the spatial propagation optical path up to the optics of inspection unit 100. This in turn enables reduction of optical-axis deviations occurring due to vibrations, thereby suppressing influenceability upon inspection processes. Another advantage of the light path length reduction is an ability to increase the use efficiency of illumination light.

Also importantly, it is revealed that the currently most preferable shortest wave length of short-wavelength light sources for high accuracy inspection using transmissive optics is about 198 nm. This indicates that optical components made of quartz are employable in optical systems. One major reason of this is that light absorption of the environmental air is negligible. In shorter wavelength regions than 198 nm, physical variations of optical components can cause undesired expansion up to an absorption edge, which might lead to risks that uniform-in-quality or "homogeneous" optical components are no longer available.

Figure 5:
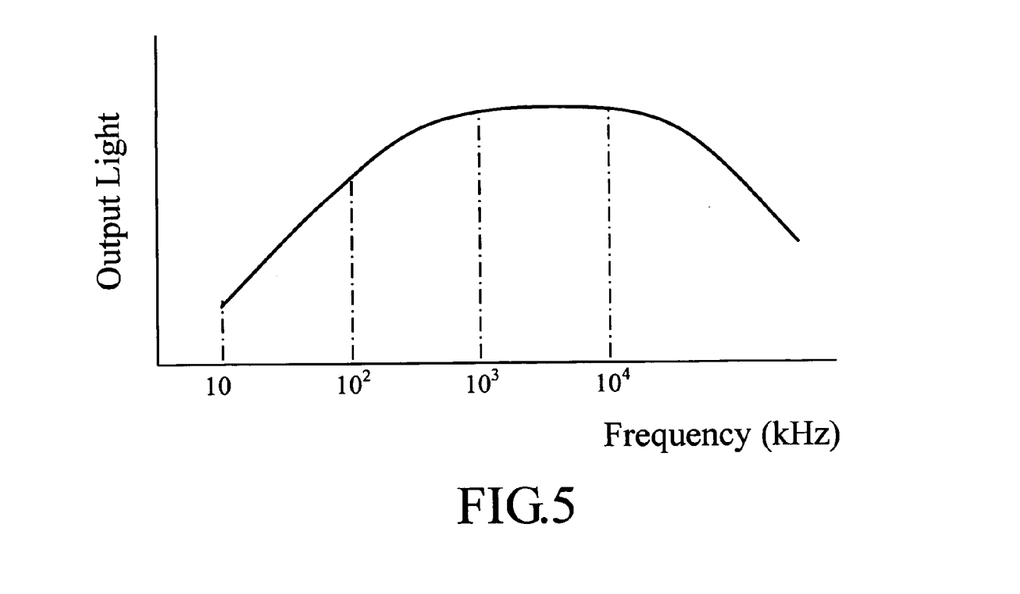
FIG. 5 is a graph showing a curve of wavelength-converted output light versus frequency.

See FIG. 5. This graph shows a curve of the light output of λ converter 330 versus the frequency of pulse drive current.

As shown in FIG. 5, it was experimentally demonstrated that the repetition frequency of output light of a DUV light source having an output required for the inspection of pattern inspection apparatus 200 is varied in a wide range of from 100 kHz to 10 MHz by changing the drive current's pulse frequency.

It was also found that the light source module embodying this invention is well adaptable for use in applications which have traditionally been believed to have no choice but to employ continuous light in charge coupled device (CCD)-aided image acquisition systems using light sources with repetition frequency of 100 kHz or higher. Practically, the light source applicability is deemed available as far as the repetition frequency of a light source is greater than or equal in value to the frame rate—i.e., a number of images capturable by image acquisition means per unit time. An example is that the PD array 105 shown in FIG. 2 is arranged to measure 10 kHz in frame rate; in this case, it is possible to overlap or superimpose together those images corresponding to ten pulses, thereby enabling achievement of ten-time averaging. Thus, the result becomes preferable as an image. The higher the light-source repetition frequency than the frame rate, the more crisp the inspection image acquired.

Using such 198-nm wavelength DUV light as the illumination light, the pattern inspection unit 100 of FIG. 1 inspects a workpiece pattern for defects.

An optical image acquisition process is as follows. The optical image acquisition unit 150 is responsive to receipt of design data containing therein graphics data indicative of graphic forms, for acquiring an optical image of a workpiece, that is, a photomask 101 with the graphic forms being drawn thereon. An exemplary procedure of the optical image acquisition will be set forth below.

The photomask 101, i.e., workpiece being tested, is mounted on the movable/rotatable table structure 102, which is driven by the X-, Y- and θ-axis motors to move in horizontal and rotation directions. The photomask 101 has on its top surface a circuit pattern, which is then irradiated with the illumination light as emitted from the wavelength (λ) converter unit 330 overlying the XYθ table 102. This unit 330 exemplifies the illumination light-use DUV light source module. The light flux as given off from the λ converter 330 travels through the illumination light optics 170 to hit the pattern-formed surface of photomask 101. The magnifying optics 104 and PD array 105 plus sensor circuit 106 are laid out to underlie the photomask 101. The light that passed through photomask 101, such as an exposure mask, progresses via the magnify optics 104 to reach PD array 105 so that a focused image is formed thereon. In order to absorb flexure of photomask 101 per se and/or vibrations of movable XYθ table 102 in Z-axis direction, a piezoelectric device 142 is used to perform image focusing on photomask 101 under the control of an automatic focusing control circuit 140.

Figure 6:
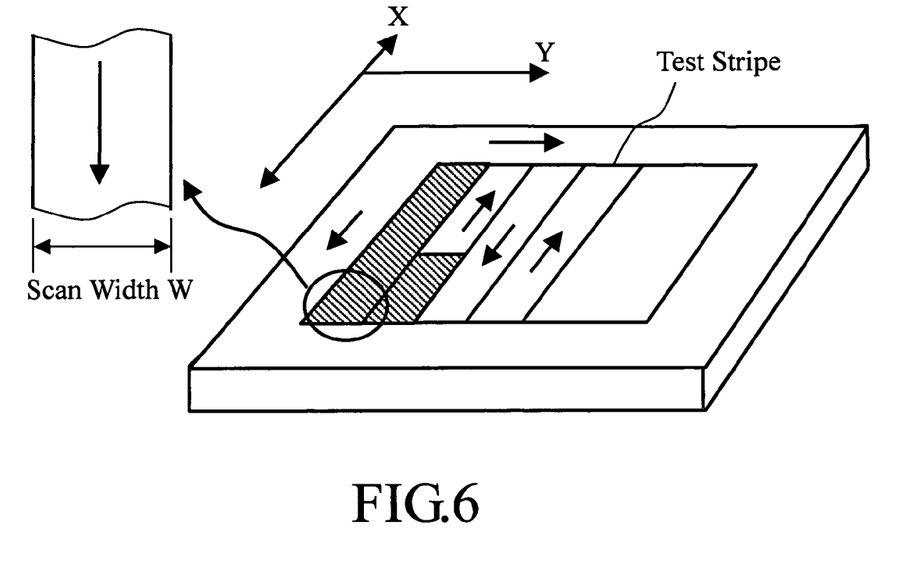
FIG. 6 shows a perspective view of a workpiece being tested, for explanation of an optical image acquisition procedure.

FIG. 6 is a diagram for explanation of the acquisition procedure of an optical image.

As shown in FIG. 6, a workpiece surface area under inspection is virtually subdivided along the Y direction into a plurality of narrow, elongate test strips each having a scan width W. The XYθ table 102 is motion-controlled to permit respective divided test strips to be scanned continuously so that an optical image is acquired during movement in the X direction. The PD array 105 is operable to seamlessly input images of the scan width W such as shown in FIG. 6. Then, after having captured the image of a first test strip, obtain the image of a second test strip while moving in the opposite direction in this event so that an image of scan width W is input in a similar way. Next, in the case of getting the image of a third test strip, image capturing is done while moving in the direction opposite to that for acquisition of the second test strip image—namely, in the same direction as that for acquisition of the first test strip image. By continuously capturing images in this serpentine manner, it is possible to shorten wasteful processing times.

The image that is focussed on the PD array 105 is photoelectrically converted thereby and is then analog-to-digital (A/D) converted by the sensor circuit 106. PD array 105 has time-delay integrator (TDI) sensors installed. By causing the XYθ table 102 for use as a workpiece support stage to move continuously in the X-axis direction, the TDI sensors pick up a circuit pattern of the photomask 101, i.e., workpiece being tested. The illumination optics 170, magnifying optics 104, PD array 105 and sensor circuit 106 along with the wavelength converter unit 330 for use as the DUV light source make up a high-power inspection optical system.

The XYθ table 102 is driven by the table control circuit 114 under control of the control computer 110. Table 102 is movable by a drive system such as three-axis (X-Y-θ) motors for driving it in the X, Y and θ directions. Examples of these X, Y and θ motors are stepper motors. A moved position of XYθ table 102 is measured by the laser-aided length measurement system 122 to generate a measurement signal, which is supplied to the position circuit 107. The photomask 101 on XYθ table 102 is automatically transported from the auto-loader 130 that is driven by the auto-loader control circuit 113 and is then automatically educed after completion of the inspection.

Measurement data (optical image data) as output from the sensor circuit 106 is sent forth toward the data distribution processor circuit 140 along with output data of the position circuit 107 indicative of a present position of the photomask 101 on XYθ table 102. The measured data may be 8-bit signless data representing the gradation or "tone" of the brightness of each pixel.

The design data used during pattern formation of the photomask 101 is stored in the magnetic disk device 109, which is an example of the storage device (storage unit).

Then, the design data is read out of magnetic disk device 109 and passed via control computer 110 to expansion circuit 111.

At an expansion step, the expander circuit 111 converts the read design data of photomask 101 for use as a workpiece being tested into two-value or multi-value image data, which will be sent forth to reference circuit 112. This circuit 112 applies appropriate filtering processing to the image data as sent thereto. It can be said that the measured pattern data indicative of an optical image as obtained by sensor circuit 106 is filtered by the resolution properties of the magnifier optics 104 and/or aperture effects or else of the PD array 105. In this state, a difference or "discrepancy" must be present between the both. Thus, filtering is also applied to the image data on the design side, thereby enabling it to be matched with the measured pattern data. In this way, a reference image for comparison with the optical image of interest is created.

At a comparison step, the comparator circuit 108 acquires the optical image (pattern image under testing) which was generated by the sensor circuit 106 based on a transmission light image obtained from the photomask 101 for use as an under-test workpiece, and the reference image (i.e., inspection reference pattern image) as generated by the expander circuit 111 and reference circuit 112, and then compares together these images in accordance with a prespecified algorithm to thereby determine whether defects are present or absent.

With such an arrangement, it is possible to achieve a highly reliable pattern inspection method using illumination light which is high in use efficiency.

Whereas the prior art requires the use of 50 kW of electric power and 50 litters per minute of cooling water on the basis of an argon laser, this embodiment is such that the use of the light source embodying the invention results in the power consumption becoming only 500 W, which is $1/100$ of the former while avoiding the need for cooling water. This coolant avoidability makes it possible to exclude contaminant production sources, such as rubber and plastic tubes or equivalents thereto. In addition, while in the prior art extra spaces have been required for installation of the light source, reservation of such extra space is no longer required in the embodiment, which is specifically arranged so that only the small-size λ converter unit 330 is installed within the non-illumination device—i.e., the body of the inspection apparatus—while letting the other part of the light source be received in the same rack as a control system of the non-illumination device. Additionally in case the non-illumination part accompanies mechanical vibrations, shockproof remedies are implemented only to the minimum part of the light source part while permitting the remaining components to be simply structured using ordinary vibration-proof schemes. This makes it possible to noticeably reduce light-source production costs.

Additionally it is possible to achieve a DUV light source which is higher in efficiency and smaller in size than the prior art, and also possible to constitute it on the basis of long lifetime semiconductor lasers and fiber amplifiers. Regarding optical components that require maintenance services at regular intervals, it is possible to receive them together in an independent housing structure.

Also importantly, the λ converter unit 330 made up of a minimal number of parts are capable of being directly built in the apparatus body while letting the optical fiber-coupled other components be installable separately at spaced-apart locations. This enables the installation device to much increase in design flexibility.

As apparent from the description above, according to this embodiment, it is possible to achieve a high-reliability pattern inspection method using a downsized light source with increased applicability and high robustness while being installable in various types of equipment as a device for emitting illumination light with its wavelength ranging from 197 to 200 nm.

Embodiment 2

So far, it was discussed in the embodiment 1 that the configuration for inspecting the pattern of a workpiece being tested while using as the illumination light from the sum frequency generation of the fourth-harmonic light of 1064-nm wavelength pulse laser light (first fundamental light) and the second-harmonic light of 1562-nm pulse laser light (second fundamental light). In an embodiment 2, another arrangement for workpiece pattern inspection will be discussed, which uses as the illumination light a beam of first summed frequency light of the fourth-harmonic light of 1064-nm wavelength pulse laser light (first fundamental light) and the 1562-nm pulse laser light (second fundamental light) and a beam of second summed frequency light using the 1562-nm pulse laser light (second fundamental light).

Figure 7:
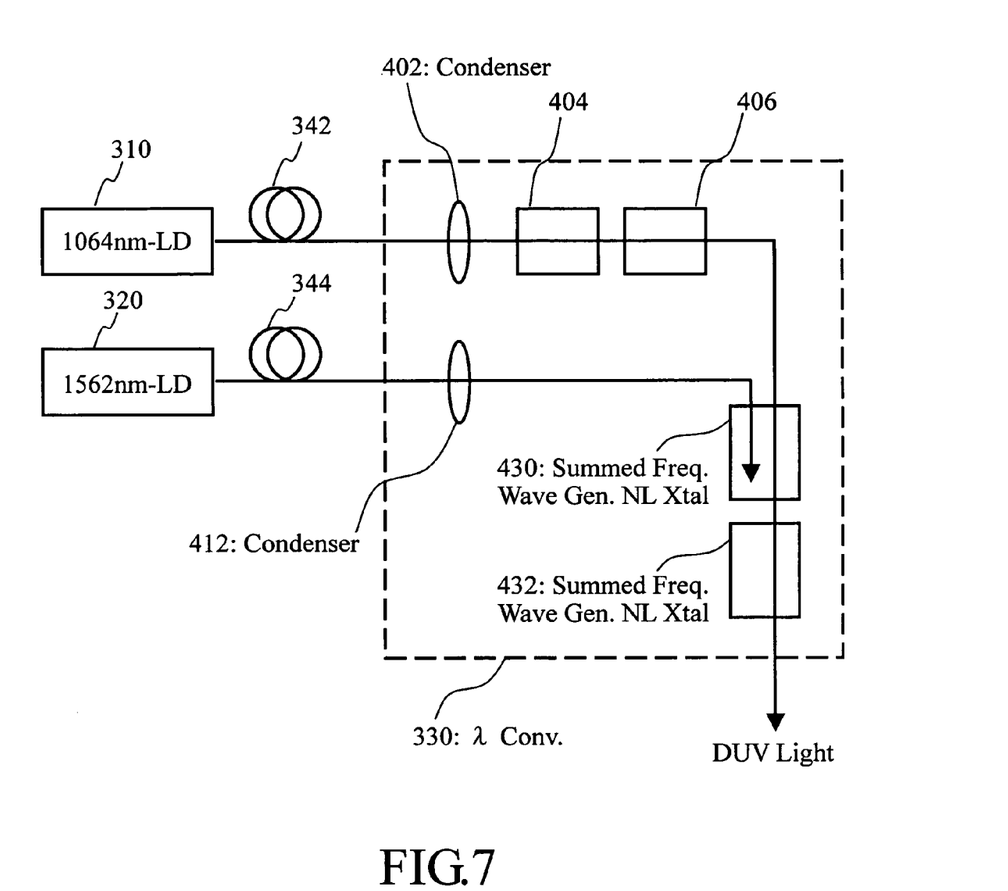
FIG. 7 shows an inside configuration of a wavelength converter unit in a light source of an embodiment 2, for explanation of the generation of illumination light.

The embodiment 2 is similar in configuration to the embodiment 1 except for the internal configuration of a wavelength (λ) converter unit 330, so repetitive explanations thereof will be eliminated herein.

FIG. 7 shows the inside arrangement of the λ converter 330 in the embodiment 2, for explanation of a technique for emitting illumination light.

In FIG. 7, a first fundamental wave light source 310 which is one example of the laser light source is arranged to emit 1064-nm wavelength laser light (first fundamental wave) as in that of the embodiment 1. For example, the first fundamental wave light source 310 is designed to have a 1064-nm light-emitting semiconductor laser diode (LD), which is indicated by "1064 nm-LD" in FIG. 7. Letting a pulsate drive current flow in light source 310 results in production of pulse laser light. Output of light source 310 is guided by an optical fiber cable 342 to reach λ converter 330.

A second fundamental wave light source 320 which exemplifies the laser light source is operable to emit 1562-nm wavelength laser light (second fundamental wave) as in the embodiment 1. For example, the second light source 320 uses a 1562-nm light-emitting semiconductor laser diode, which is labeled by "1562 nm-LD" in FIG. 7. Letting a pulsed drive current flow in second light source 320 results in creation of pulse laser light. By driving it in a similar way to the above-stated 1064 nm-LD, it was possible to provide the intended operability with jitters of 120 ps or less. Output of light source 320 is transferred by its associated optical fiber cable 344 toward the λ converter 330.

The λ converter 330 is an example of the deep ultraviolet (DUV) light source, which is arranged to emit by wavelength conversion DUV light with its wavelength of 198 nm based on the 1064-nm wavelength laser light and 1652-nm laser light. Practically the wavelength conversion is performed in a way which follows.

Firstly, fourth-harmonic wave light is generated. The incoming 1064-nm laser light from the optical fiber 342 is collected by a condenser lens 402, resulting in an increase in electrical field. This permits the light to enter a nonlinear crystal 404, which is for creation of second harmonic wave of the 1064-nm wavelength laser light, thereby producing laser light with its wavelength of 532 nm, which is for use as the second harmonic wave of the 1064-nm wavelength laser light. Then, guide this 532-nm wavelength laser light to enter a nonlinear crystal 406, which is for generation of fourth harmonic wave, resulting in production of laser light having a wavelength of 266 nm, which becomes the fourth harmonic wave of the 1064-nm wavelength laser light. Preferably the second harmonic wave-producing nonlinear crystal 404 is made of potassium titanyl phosphate ($KTiOPO_4$ or KTP), whereas the fourth harmonic wave creating nonlinear crystal 406 is made of beta barium borate ($\beta\text{-}BaB_{24}$ or BBO), although any other similar suitable crystal materials are employable as far as these are transparent at the wavelength of interest and offer phase matchablilities in respective wavelength conversion processes.

Within the λ converter unit 330, the above-noted wavelength conversion proceeds to a further process for letting the 266-nm wavelength laser light, which is the fourth harmonic wave light of the 1064-nm wavelength light, be reflected by the optics including a reflector mirror (not shown) and then coaxially enter to the summed frequency generation-use nonlinear crystal 430 in the form of a single beam of collected light along with the 1562-nm wavelength laser light, resulting in creation of 277-nm wavelength laser light having a summed frequency of the both. Letting it enter as the single beam of collected light enables the conversion efficiency to increase. Preferably the nonlinear crystal 320 as used here may be made of BBO, although other similar materials are employable as far as these are optically transparent relative to this wavelength while offering phase matchability during the wavelength conversion process. Examples of such materials are LBO and CLBO.

In λ converter 330, the above-noted wavelength conversion further proceeds to a process for letting the 266-nm wavelength laser light and 1562-nm wavelength laser light coaxially enter a summed frequency generating nonlinear crystal 432 in the form of a single beam of collected light, resulting in production of 198-nm wavelength laser light with a summed frequency of the both. Preferably the nonlinear crystal 430 used here may be made of BBO, although other similar materials employable as far as these are transparent relative to this wavelength while offering phase matchability during the wavelength conversion process. An example of such materials is CLBO. Then, let the 198-nm wavelength laser light enter the illumination optics 170 as the illumination light of pattern inspection apparatus 200, for performing inspection of the pattern of a photomask 101 in the way stated previously.

Although in the context here the explanation and illustration of the optics such as a total reflection mirror for varying the optical path of the laser light are simplified, it is readily occur to those skilled in the art that any appropriate optics may be used to vary the laser light optical path.

It has been stated that with the arrangement of the embodiment 2 also, it is possible to obtain similar effects and advantages to those of the embodiment 1.

As apparent from the foregoing, in accordance with the pattern inspection apparatus embodying the invention, it is possible by use of the optical fibers to successfully separate the laser light source and illumination light source. This makes it possible to downsize the illumination light source, thereby permitting it to be built in the pattern inspection unit. Thus it is possible to shorten the spatial propagation optical path, which leads to an ability to lessen vibration influenceability during pattern inspection. It is also possible for the pattern inspection apparatus embodying the invention to use as its illumination light the laser light having a wavelength of DUV region.

System elements which are expressed by the terms "circuits" or "steps" in the description above may be arranged by computer-executable software programs. When the need arises, these may alternatively be implemented not only by software programs but also by use of hardware and software combinations. Similar results are also obtainable by designing them in a combination with firmware. In the case of the arrangement using programs, the programs are prestored in nondestructive recording media, such as magnetic disks, magnetic tapes, floppy diskettes (FDs), read-only memories (ROMs) or equivalents thereto. For example, those circuits making up the arithmetic control unit in the workpiece inspection apparatus 100—namely, the table control circuit 114, expander circuit 111, reference circuit 112, comparator circuit 108, etc.—may be configured from electrical circuitry or alternatively realized in the form of software programs capable of being executed by the control computer 110. Still alternatively, these circuits may be implemented in the form of combinations of electrical circuitry and software programs.

While this invention has been particularly shown and described with reference to specific embodiments, the invention should not exclusively be limited thereto. For instance, each embodiment stated supra may be designed to use reflected light in place of the transmitted light or alternatively employ both the transmitted light and reflected light at a time. Although the reference image for use as the under-test pattern data is produced from the design data, similar results are obtainable by using the data of identical pattern as sensed or "captured" by an image sensor including a PD array or else. In other words, similar results are obtainable irrespective of whether the embodiment is applied to die-to-die inspection or die-to-database inspection.

Although in each embodiment the XYθ table 102 is designed to move for enabling the scanning of an inspection position, the XYθ table may be immovably designed while permitting other optics to move relatively. Additionally, while in each embodiment the outgoing illumination light of the wavelength converter unit 330 is arranged to form the top-down optical path, this design should not be interpreted to limit the invention and may be modified so that the optical path is formed along other directions in accordance with the optics arranged in the inspection system.

Additionally, although detailed explanations are omitted as to those components which are not specifically required for the description of this invention, such as device configuration and control schemes or else, it is possible to selectively use any required device configurations and control schemes on a case-by-case basis.

It should be appreciated that for miscellaneous matters, any variants of the pattern inspection apparatus or the light source device for use therein are construed to be involved in the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus, comprising:
   a first laser light source configured to emit first laser light having a first wavelength;
   a second laser light source configured to emit second laser light having a second wavelength different from the first wavelength;
   a wavelength conversion unit configured to convert the first laser light to a fourth harmonic wave of the first laser light, to generate first summed frequency light from the fourth harmonic wave of the first laser light and from the second laser light, and to generate second summed frequency light from the first summed frequency light and the second laser light as deep ultraviolet light with a wavelength of less than or equal to 266 nm;
   a first optical fiber configured to connect said first laser light source and said wavelength conversion unit;
   a second optical fiber configured to connect said second laser light source and said wavelength conversion unit; and a pattern inspection unit with said wavelength conversion unit built therein, the pattern inspection unit configured to inspect a pattern of a workpiece being tested while using as illumination light the deep ultraviolet light as emitted from said wavelength conversion unit.

2. A pattern inspection apparatus, comprising:

a first laser light source configured to emit first laser light having a first wavelength from 1064 to 1065 nm;

a second laser light source configured to emit second laser light having a second wavelength from 1557 to 1571 nm;

a wavelength conversion unit configured to convert the first laser light to a fourth harmonic wave of the first laser light having the wavelength from 1064 to 1065 nm, to convert the second laser light to a second harmonic wave of the second laser light having the second wavelength from 1557 to 1571 nm, and to generate a summed frequency light from said fourth harmonic wave of the first laser light and from said second harmonic wave of the second laser light as deep ultraviolet light with a wavelength of less than or equal to 266 nm;

a first optical fiber configured to connect said first laser light source and said wavelength conversion unit;

a second optical fiber configured to connect said second laser light source and said wavelength conversion unit; and a pattern inspection unit with said wavelength conversion unit built therein, the pattern inspection unit configured to inspect a pattern of a workpiece being tested while using as illumination light the deep ultraviolet light as emitted from said wavelength conversion unit.

3. The apparatus according to claim 1, wherein said first laser light source is configured to generate the first laser light having the first wavelength ranging from 1,064 to 1,065 nm, and the second laser light source is configured to emit the second laser light having the second wavelength from 1557 to 1571 nm.

4. The apparatus according to claim 1, wherein said wavelength conversion unit comprises a nonlinear crystal configured to emit the fourth harmonic wave of said first laser light, said nonlinear crystal including potassium phosphate titanate ($KTiOPO_4$ or "KTP") and beta barium borate ($\beta$-$BaB_2O_4$ or "BBO").

5. The apparatus according to claim 2, wherein said wavelength conversion unit comprises a nonlinear crystal configured to emit the second harmonic wave of said second laser light, said nonlinear crystal including lithium triborate ($LiB_3O_5$ or "LBO").

6. The apparatus according to claim 1, wherein said first optical fiber comprises a quartz fiber with ytterbium (Yb) doped thereinto as an active material.

7. The apparatus according to claim 1, where said second optical fiber comprises a quartz fiber with erbium (Er) doped therein as an active material.

8. A pattern inspection apparatus, comprising:

a first laser unit configured to emit first laser light having a first wavelength;

a second laser unit configured to emit second laser light having a second wavelength different from the first wavelength;

means for converting the first laser light to a fourth harmonic wave of the first laser light, for generating first summed frequency light from the second laser light and the fourth harmonic wave of the first laser light, and for generating second summed frequency light from the first summed frequency light and the second laser light as deep ultraviolet light with a wavelength of less than or equal to 266 nm;

a first connecting unit configured to connect said first laser unit and said means for converting;

a second connecting unit configured to connect said second laser unit and said means for converting; and means for inspecting a pattern of a workpiece being tested while using as illumination light the deep ultraviolet light as emitted from said means for converting, said means for converting is built within said means for inspecting.

9. A method, comprising:

emitting first laser light having a first wavelength;

emitting second laser light having a second wavelength different from the first wavelength;

generating a fourth harmonic wave of the first laser light;

generating first summed frequency light from the second laser light and the fourth harmonic wave of the first laser light;

generating second summed frequency light from the first summed frequency light and the second laser light as deep ultraviolet light with a wavelength of less than or equal to 266 nm; and inspecting a pattern of a workpiece being tested with the deep ultraviolet light as illumination light.

10. The apparatus according to claim 1, wherein said pattern inspection unit comprises:

a housing including at least one optical lens, at least one mirror, and a scanner.

11. The apparatus according to claim 10, wherein said housing includes said wavelength conversion unit.

12. The apparatus according to claim 10, wherein said wavelength conversion unit is integrally combined with said housing.

13. The apparatus according to claim 1, wherein said wavelength conversion unit does not include a resonator.

14. The apparatus according to claim 1, wherein said pattern inspection unit includes a photodiode array.

15. The apparatus according to claim 14, wherein said photodiode array is configured to image said workpiece at 10 kHz.

16. The apparatus according to claim 1, wherein said second laser light source is configured to emit said second laser light with jitters of 120 picoseconds or less.

* * * * *